United States Patent [19]

Mitchell et al.

[11] 4,393,235

[45] Jul. 12, 1983

[54] PROCESS FOR PRODUCING P-HYDROXYPHENYL/ACETIC ACID

[75] Inventors: Alan Mitchell, Macclesfield; Thomas Bailey, Bramhall, both of England

[73] Assignee: Imperial Chemical Industries PLC, London, England

[21] Appl. No.: 259,925

[22] Filed: May 4, 1981

[30] Foreign Application Priority Data

Jun. 11, 1980 [GB] United Kingdom ............... 8019155

[51] Int. Cl.$^3$ .......................................... C07C 65/01
[52] U.S. Cl. ..................................... 562/478; 564/182
[58] Field of Search ....................... 562/478; 564/182

[56] References Cited

U.S. PATENT DOCUMENTS 4,198,526  4/1980  Edwards .............................. 562/478

FOREIGN PATENT DOCUMENTS 54-76542  6/1979  Japan .................................. 562/478

Primary Examiner—Paul J. Killos
Attorney, Agent, or Firm—Cushman, Darby & Cushman

[57] ABSTRACT

A process for the preparation of p-hydroxyphenylacetic acid by reducing p-hydroxymandelic acid with a stannous salt. The product is a valuable intermediate for the preparation of the β-adrenergic blocking agent atenolol.

5 Claims, No Drawings

PROCESS FOR PRODUCING P-HYDROXYPHENYL/ACETIC ACID

This invention relates to a new chemical process and more particularly it relates to an improved process for the reduction of p-hydroxymandelic to p-hydroxyphenylacetic acid.

In United Kingdom Specification No. 1,576,333 (U.S. Pat. No. 4,198,526 corresponds) there are described various methods for carrying out the abovementioned reduction, and the preferred method is stated to be a process using a chromous salt. This is indeed a very effective process which gives high yields on a commercial plant scale, but it suffers from a number of practical disadvantages. Firstly, it is a heterogeneous reaction because the chromous salt is most conveniently prepared in situ using a chromic salt and suspended zinc dust, and this requires careful attention to the surface properties and agitation of the zinc. Secondly, on plant scale it produces a large and variable exotherm, requiring careful monitoring of the reaction. Thirdly, and most important of all, the chromium and zinc residues from the process cannot satisfactorily be recovered for re-use, and their disposal produces an environmental problem.

We have now found, and herein lies our invention, a process for carrying out the said reduction which overcomes the abovementioned disadvantages.

According to the invention there is provided a process for the manufacture of p-hydroxyphenyl-acetic acid which comprises the reduction of p-hydroxymandelic acid with a stannous salt under acidic conditions.

The reaction is preferably carried out in aqueous solution in the presence of a mineral acid, for example hydrochloric acid, at a temperature of up to 100° C., preferably at 80°-85° C.

The p-hydroxymandelic acid used as starting material is most conveniently provided in the form of the monohydrate of its sodium salt, which is described in United Kingdom Specification No. 1,576,331 (U.S. Pat. No. 4,198,525 corresponds).

p-Hydroxyphenylacetic acid is a valuable intermediate for the preparation of the $\beta$-adrenergic blocking agent atenolol.

The invention is illustrated but not limited by the following Example:

EXAMPLE 1

Aqueous 11 N-hydrochloric acid (1200 liters) is added to a stirred mixture of water (1200 liters) and sodium p-hydroxymandelate monohydrate (760 kg.). Stannous chloride dihydrate (910 kg.) is added and the stirred mixture is heated at 80°-85° C. for 1 hour and then cooled to 10° C. and filtered. The solid residue is dried and there is thus obtained p-hydroxyphenylacetic acid (550 kg.).

In general the p-hydroxyphenylacetic acid is not dried and isolated in solid form, but converted into p-hydroxyphenylacetamide by the following procedure:

The above acid as a wet paste from the filter (550 kg. dry weight) is dissolved in isobutyl methyl ketone (1000 liters) and heated to give a vapour temperature of 105° C. at atmospheric pressure, when an azeotropic mixture of water and isobutyl methyl ketone distils off. When all the water has been removed the solution is cooled to 10° C., and methanol (750 liters) and 11 N- aqueous hydrochloric acid (10 liters) are added. The mixture is heated under reflux for 4 hours, and the solvents are then removed by evaporation under reduced pressure (50 mm. Hg.) at an internal temperature of 100° C. The residue is cooled to 10° C., aqueous ammonium hydroxide solution (1250 liters; specific gravity 0.880) is added and the mixture is stirred at 20°-25° C. for 14 hours. The excess of ammonia is removed by distillation at an internal temperature of 100° C. and the residue is cooled to ambient temperature. The mixture is filtered and the solid residue is washed twice with cold water (200 liters each time) and air-dried at 80° C. There is thus obtained p-hydroxyphenylacetamide (420 kg.)

What we claim is:

1. A process for the manufacture of p-hydroxyphenylacetic acid which comprises reducing p-hydroxymandelic acid with a stannous salt under acidic conditions, the reduction being carried out in aqueous solution in the presence of a mineral acid at a temperature of up to 100° C.

2. A process as claimed in claim 1 wherein the mineral acid is hydrochloric acid.

3. A process as claimed in claim 2 which is carried out at a temperature of between 80° and 85° C.

4. A process as claimed in claim 1 wherein the p-hydroxymandelic acid used as starting material is provided in the form of the monohydrate of its sodium salt.

5. A process as claimed in claim 1 wherein the stannous salt is stannous chloride and the p-hydroxyphenylacetic acid is obtained in the form of a wet paste which is converted directly to p-hydroxyphenylacetamide without first drying and isolating the p-hydroxyphenylacetic acid.

* * * * *